US00PP32370P2

(12) United States Plant Patent
Hansen

(10) Patent No.: US PP32,370 P2
(45) Date of Patent: Oct. 20, 2020

(54) ***AGAVE* PLANT NAMED 'BLUE IVORY'**

(50) Latin Name: *Agave gypsophila*
Varietal Denomination: Blue Ivory

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/873,125

(22) Filed: Feb. 5, 2020

(51) Int. Cl.
*A01H 5/12* (2018.01)

(52) U.S. Cl.
USPC ..... Plt./373

(58) Field of Classification Search
USPC ..... Plt./373
CPC ..... A01H 5/12
See application file for complete search history.

*Primary Examiner* — Annette H Para

(57) ABSTRACT

A new and unique *Agave* plant named 'Blue Ivory' characterized by low mounded plant habit of long, linear, slightly-folded, distally-reflexed, variegated leaves having wide creamy-white margins with bluish-green centers and light bluish-green blush in the intermediate region. The leaves have firm, sharp medium-sized marginal and small apical spines and show occasional imprints from marginal spies of leaves above or below. The plant is useful in the landscape as a specimen, en masse, or also in a container in the home or landscape.

2 Drawing Sheets

Botanical classification: *Agave gypsophila.*
Variety denomination: 'Blue Ivory'.

BACKGROUND OF THE INVENTION

The present invention relates to the new and distinct *Agave* plant, *Agave* 'Blue Ivory' discovered by the inventor at a wholesale perennial nursery in Zeeland, Mich., USA as an uninduced whole-plant mutation from a tissue cultured crop of *Agave* 'Ivory Curls' (not patented) on Jun. 14, 2016. Prior to assigning the new plant a cultivar name, the new plant was identified through the evaluation process with the code 16-Sp-Agav-493. The new plant has been successfully asexually propagated by offset division at a wholesale perennial nursery in Zeeland, Mich. Offset division propagation has been found produce stable and identical plants that maintain the unique characteristics of the original plant.

No plants of *Agave* 'Blue Ivory' have been sold, in this country or anywhere in the world, prior to the filing of this application, nor has any disclosure of the new plant been made prior to the filing of this application with the exception of that which was disclosed within one year of the filing of this application and was either derived directly or indirectly from the inventor.

BRIEF SUMMARY OF THE INVENTION

*Agave* 'Blue Ivory' is a sport of 'Ivory Curls' which is a selection of *Agave gypsophila*. 'Blue Ivory' differs from its parent, 'Ivory Curls', as well as all other *Agaves* known to the applicant. The most similar known *Agave* cultivar other than the parent is 'Lover Boy' (not patented). 'Lover Boy' has foliage that is light chartreuse and becomes more greenish-white with intense light. 'Ivory Curls' has leaf margins that narrower and have a light bluish-green blush rather than the clearer creamy-white margins of the new plant. 'Ivory Curls' also has marginal teeth that are darker and more folding and reflex curling in the distal portion of the leaves.

*Agave* 'Blue Ivory' differs from all other *Agaves* known to the applicant, by the combination of the following traits:

1. Long, variegated, slightly-folded leaves with marginal teeth;
2. Leaves have wide creamy-white margins and contrasting bluish-green leaf centers with a light bluish-green blush in between the margin variegation and in center;
3. Leaves are slightly reflexed toward the distal region;
4. Leaves show occasional imprints or indentations on adaxial and abaxial surfaces from marginal teeth on leaves above or below;
5. Habit is mounded with mostly outright to horizontal foliage.

BRIEF DESCRIPTION OF THE DRAWINGS

The photograph of the new plant demonstrates the overall appearance of the new plant including the unique traits as a two-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
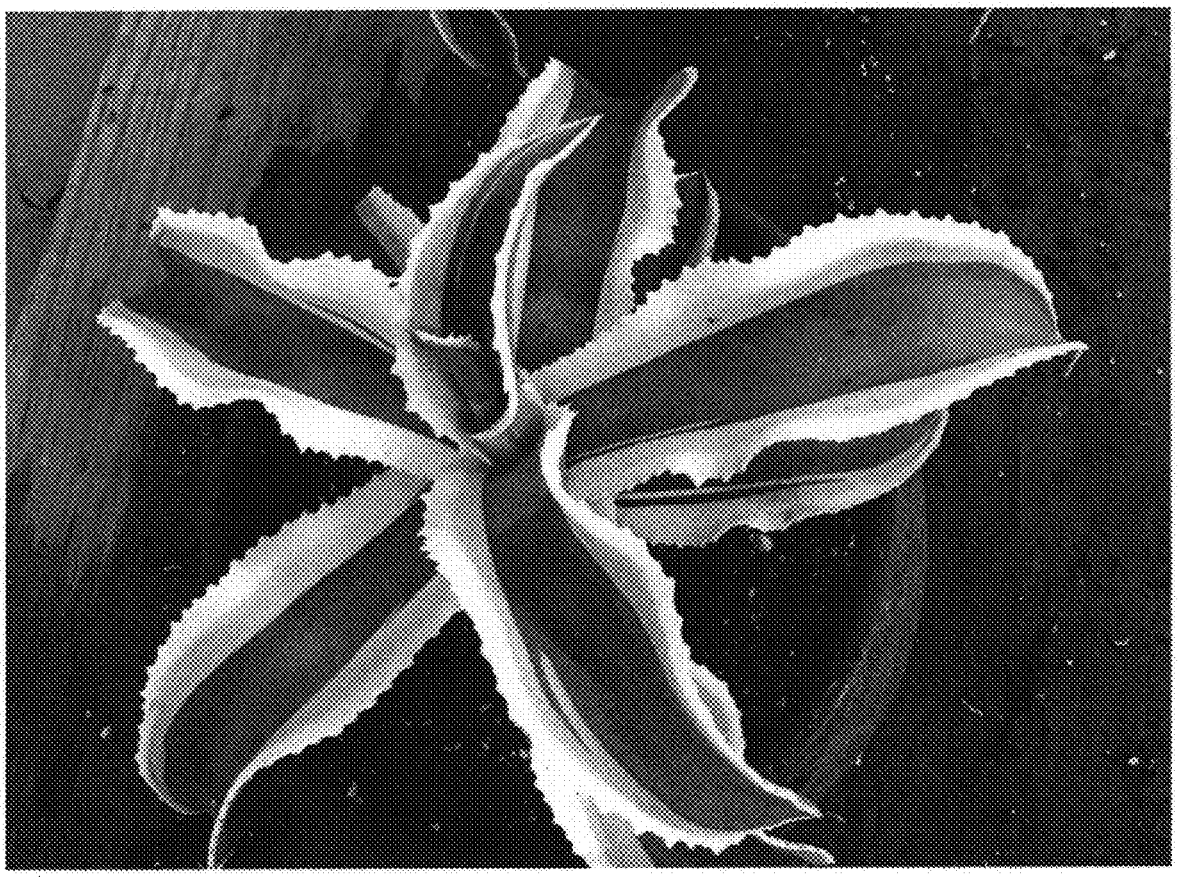
FIG. 1 shows a close-up of the new plant in a container with new unfurling foliage and marginal teeth and apical spines.
Figure 2:
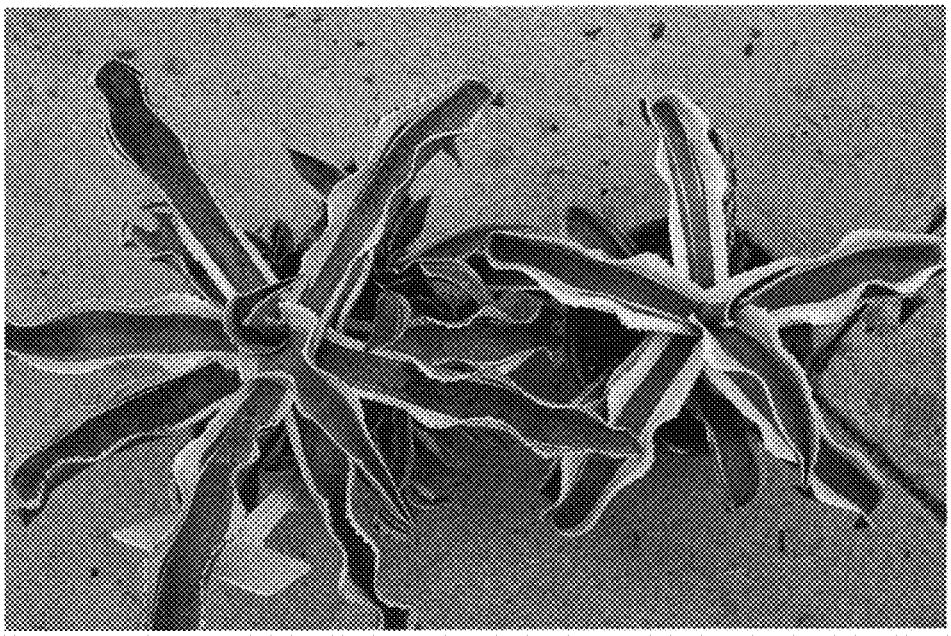
FIG. 2 shows a comparison of the variegation color and width, and the habit of the new plant (on the right) and the sport parent, 'Ivory Curls' (on the left).
Figure 3:
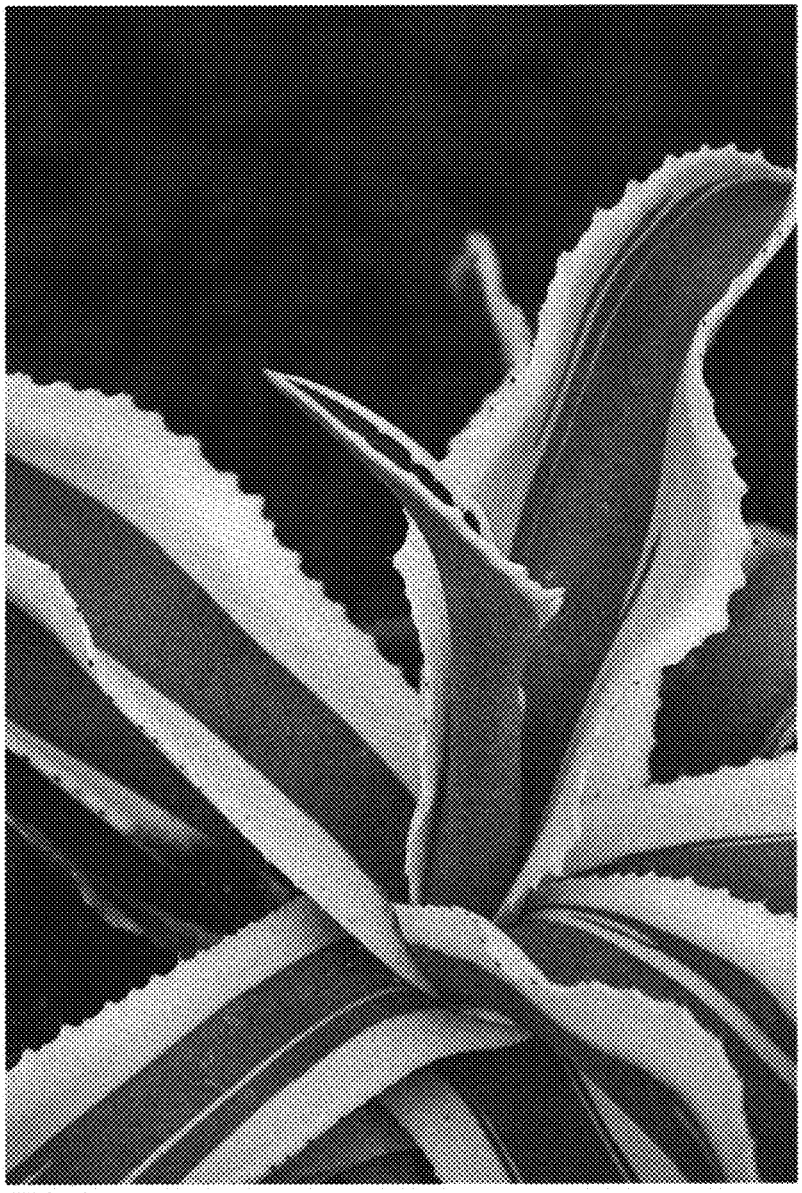
FIG. 3 shows a close-up of the leaves with teeth imprints and marginal teeth.

The following descriptions and color references are based on the 2015 edition of The Royal Horticultural Society Colour Chart except where common dictionary terms are used. The new plant, *Agave* 'Blue Ivory', has not been observed under all possible environments. The phenotype may vary slightly with different environmental conditions, such as temperature, light, fertility, moisture and maturity levels, but without any change in the genotype. The following observations and size descriptions are of a three-year-old plant in a commercial wholesale greenhouse in Zeeland, Mich. with supplemental water and fertilizer as needed.

Botanical classification: *Agave gypsophila;*

Variety denomination: 'Blue Ivory';

Sport parentage: Uninduced whole-plant sport of *Agave* 'Ivory Curls';

Propagation: Division of offsets and shoot tip tissue culture;

Time to initiate roots: About 42 days;

Growth rate: Moderate to slow;

Crop time: About 20 weeks to finish during the summer in a 3.8 liter container from an established offset;

Rooting habit: Fleshy, lightly branching, with roots up to 20 cm long;

Root color: Nearest RHS 158C;

Plant shape and habit: Herbaceous tender perennial with basal rosettes of narrow, slightly folded, sinuate, distally reflexed, variegated, whorled leaves emerging from central base, producing a low symmetrical mound;

Plant size: Foliage height about 10.3 cm tall from soil line to the top of the leaves and about 22.0 cm wide at the widest point about slightly below soil line when grown in containers;

Foliage description: Linear; simple; sarcous; narrowly acute apex ending in medium-length stiff spine; truncate sessile base; marginal, outwardly-pointing, sharp, stiff spines decreasing slightly in size in proximal portion; slightly folded; glabrous, scabrous and slightly glaucous adaxial and abaxial; attitude mostly outwardly with distal portion reflexed;

Number of leaves: About 20 per plant;

Leaf size: To about 34.3 cm long, 8.9 cm wide near middle and 25 mm thick near base; average 32.5 cm long, 8.5 cm wide near middle and 23 mm thick near base;

Leaf variegation dimensions: Adaxial margin to 16.0 mm wide in longitudinal middle and tapering rapidly to about 2.0 mm near apex; abaxial margin to about 16.0 mm in longitudinal middle and tapering rapidly to about 1.0 mm wide at apex; adaxial intermediate zone between creamy-white margins and bluish-green center widest in longitudinal center to about 5.4 mm wide, abaxial intermediate zone to about 6.0 mm wide; adaxial bluish-green center to about 2.2 cm wide in middle; abaxial bluish-green center about 6.8 cm wide; with irregular narrow longitudinal stripes of bluish-green extending various random lengths into the intermediate zone and narrow creamy-white longitudinal stripes of various random lengths extending into the blue- green centers of mostly on adaxial and rarely on abaxial;

Foliage fragrance: None observed;

Stem: To about 6.4 cm wide and about 5.0 cm tall; covered with leaves;

Leaf blade color:

*Mature adaxial*.—Outer margin nearest RHS NN155A, center nearest a blend between RHS 136A and RHS 190B, intermediate zone nearest a blend between RHS N155A and RHS 133B.

*Mature abaxial*.—Margin nearest RHS NN155A, center nearest a blend between RHS 136A and RHS 190A; intermediate zone nearest blend between RHS 136B and RHS NN155A.

*Expanding young adaxial*.—Margin nearest RHS NN155, center nearest a blend between RHS 136A and RHS 190C, intermediate zone nearest RHS N155A and RHS 136B.

*Expanding young abaxial*.—Margin between RHS NN155A to N155D, center blending between RHS 122C, RHS 190B and RHS N155A; intermediate zone a blending of nearest RHS NN155A and RHS 136B.

Apical spine: Stiff and sharp; to about 2.5 mm long, about 1.0 mm across at base;

Apical spine color: Nearest RHS 200A;

Marginal spines: Sharply pointed; stiff; distally pointing outwardly and slightly curved toward apex or base; lighter colored and decreasing in size, stiffness and separation in proximal portion; distally about 4.5 mm long and about 7.5 mm apart; proximally about 2.0 mm long and 5.0 mm apart;

Marginal spine color: On young emerging leaves and basal 2 cm of mature leaves nearest RHS NN155A, distally on mature leaves nearest RHS 200A with tips nearest RHS 164A;

Petiole: Sessile;

Veins: Absent;

Flower description: Flowers have not yet been observed;

Fruit and seed: Have not yet been observed;

Disease resistance: *Agave* 'Blue Ivory' has not been observed to be resistant to diseases common to *Agaves* beyond that which is normal for *Agave*. The plant is xeromorphic and survives well with minimal water once established. Hardy in frost-free areas. Full extent of winter hardiness has not been tested.

I claim:

1. A new and distinct cultivar of ornamental *Agave* plant named 'Blue Ivory' as herein described and illustrated.

* * * * *